United States Patent [19]

Bankwitz et al.

[11] Patent Number: 5,599,968
[45] Date of Patent: Feb. 4, 1997

[54] CONTINUOUS PROCESS FOR THE PREPARATION OF ORGANIC ISOCYANATES

[75] Inventors: Robert Bankwitz, Kempen; Herbert Gebauer, Krefeld; Christian König, Kaarst; Eckart Waldau, Düsseldorf, all of Germany

[73] Assignee: Bayer Aktiengesellschaft, Leverkusen, Germany

[21] Appl. No.: 566,531

[22] Filed: Dec. 4, 1995

[30] Foreign Application Priority Data

Dec. 8, 1994 [DE] Germany ............... 44 43 642.4

[51] Int. Cl.$^6$ ............................................. C07C 263/10
[52] U.S. Cl. ............................................. 560/347
[58] Field of Search ................................... 560/347

[56] References Cited

U.S. PATENT DOCUMENTS

| | | | |
|---|---|---|---|
| 2,875,225 | 2/1959 | Böhme et al. | 260/453 |
| 3,781,320 | 12/1973 | Irwin | 260/453 PH |
| 3,829,458 | 8/1974 | Horn et al. | 260/453 PH |
| 3,947,484 | 3/1976 | Mitrowsky et al. | 260/453 PH |
| 4,128,569 | 12/1978 | Horn et al. | 260/453 PH |
| 4,297,501 | 10/1981 | Becker et al. | 560/24 |
| 4,419,295 | 12/1983 | Hennig et al. | 260/453 PH |
| 4,422,976 | 12/1983 | Yamamoto et al. | 260/453 PH |
| 4,851,570 | 7/1989 | Zaby et al. | 560/347 |
| 5,117,048 | 5/1992 | Zaby et al. | 560/347 |

FOREIGN PATENT DOCUMENTS

| | | |
|---|---|---|
| 1037444 | 8/1958 | Germany . |
| 2058032 | 5/1972 | Germany . |

*Primary Examiner*—Samuel Barts
*Attorney, Agent, or Firm*—Joseph C. Gil; N. Denise Brown

[57] ABSTRACT

Organic isocyanates are continuously prepared by reacting primary organic amines with phosgene in the presence of an inert, organic solvent, with the reaction mixture being circulated by means of a bubble column at a temperature of from 60° to 100° C. and with the ratio of the quantity of the circulated amine reaction products to the quantity of the amine supplied of from 100:1 to 5:1.

5 Claims, No Drawings

CONTINUOUS PROCESS FOR THE PREPARATION OF ORGANIC ISOCYANATES

BACKGROUND OF THE INVENTION

The present invention relates to a continuous process for the preparation of organic isocyanates by reacting primary organic amines with phosgene in an organic solvent at temperatures of from 60° to 100° C., wherein the reaction mixture is circulated by means of a bubble column.

The continuous preparation of organic isocyanates by reacting primary organic amines with phosgene in an organic solvent is frequently described and is carried out on a large scale (see, for example, Ullmanns Enzyklopädie der Technischen Chemie, 4th Edition, Volume 13; Kunststoffhandbuch, Volume 7 (Polyurethane), 3rd revised Edition, Carl Hanser Verlag, Munich, Vienna, page 76 (1993). The course of the reaction is, in most cases, separated into two temperature steps, the cold and the hot phosgenation. In the first step, the amine is reacted with phosgene in a rapid exothermic reaction at low temperatures to form a mixture of carbamic acid chloride and amine hydrochloride. This reaction mixture is then "completely phosgenated" at elevated temperatures, until the evolution of gas has stopped. A satisfactory yield is achieved in this process through the large excess of phosgene, through the dilution of the co-reactants using a large amount of an organic solvent, and through the two-step reaction procedure (cold and hot phosgenation).

The disadvantage of this process is the high energy consumption, which is necessary due to the recovery and purification of the solvent and the excess phosgene. For this reason, there have been many attempts to improve the phosgenation process.

Thus, in the patent literature a series of processes is described in which the purpose is to ensure a very efficient, thorough mixing of the starting components reacted together—primary amine and phosgene—with circulation apparatus and/or dynamic or static mixers being used. By this means, it is possible to operate at a higher concentration (less solvent) and using a lower phosgene excess, with the same yield being obtained. For example, German Offenlegungsschrift 2,212,181 describes a process in which intimate mixing is achieved by pumping the liquid reaction mixture together with the gaseous reaction products cocurrently in a recycle loop through a packed column at a rate such that a so-called transition flow having turbulent properties develops in the packed column. German Offenlegungsschrift 2,624,285 describes a process whereby the reaction mixture together with the liquid phosgene are pumped in a recycle loop through a jet nozzle, with a solution of the amine being fed to this nozzle in such a way that a reaction and mixing zone having a high energy dissipation density is formed. Another circulation process is described in German Offenlegungsschrift 3,212,510. In this patent, the process is operated under pressure at a temperature such that 30 to 70% of the carbamic acid chloride formed in the first reaction step is decomposed into isocyanate, so a low-viscosity mixture is produced, which can be pumped around at a high velocity. In U.S. Pat. No. 3,781,320, a circulation apparatus is described for the preparation of organic isocyanates from primary amines and phosgene, wherein a mixing unit having a higher shearing action is employed.

The process for the phosgenation of amines in a circulation apparatus is described in the German patent 1,037,444. Here, the mixing of the co-reactants takes place under pressure and at a temperature higher than the decomposition temperature of the carbamic acid chloride. Since the separation of hydrogen chloride and excess phosgene occurs at low pressure, a pump having a suitable delivery head is used. Several of the previously known processes using circulation apparatus have the disadvantage, however, that they are operated at temperatures at which the carbamic acid chloride formed in the first reaction step is to a great extent partially or completely decomposed into isocyanate and hydrogen chloride and where the free isocyanate competes so strongly with phosgene during the reaction of the amine that ureas are formed. These formed ureas are no longer completely converted to isocyanate but lead to by-products which diminish the yield of isocyanate and/or impair the quality of the product.

In other phosgenation processes, attempts are made to achieve the desired intensive, thorough mixing by means of dynamic or static mixers in a single passage, that is, without circulation. Thus, German Offenlegungsschrift 2,153,268 describes the reaction of primary amines with phosgene in organic solvents in multistage centrifugal pumps and German Offenlegungsschrift 3,121,036 describes the same reaction in a smooth jet nozzle.

Another way, at least of lowering the phosgene excess used, is phosgenation under pressure. To ensure an economic production output, all large-scale processes for the preparation of organic isocyanates by phosgenation of primary amines operate at elevated temperatures. The solubility of the phosgene in the reaction mixture and with it, the active phosgene excess are decreased in this process. An increased reactor pressure counteracts this. Apart from the fact that the high dilution necessary for a good yield is not decreased during these processes, large-scale pressure apparatuses are very expensive and present problems due to the high toxicity of phosgene.

The carrying out of the phosgenation reaction under pressure also has the disadvantage that, besides the phosgene concentration, the HCl concentration also increases in accordance with Henry's law and the formation of amine hydrochloride is thereby favored. The advantage of the higher phosgene concentration in connection with the reaction rate is completely or partially offset thereby, as the reaction of amine hydrochloride with phosgene is the rate-determining step in any phosgenation process for the preparation of isocyanates.

All the previously known processes for the reaction of primary amines with phosgene in circulation apparatus have moreover the disadvantage that pumps are required for the circulation.

SUMMARY OF THE INVENTION

The process of the invention is directed to the preparation of organic isocyanates in high yield from the reaction of primary amines with phosgene, wherein a concentrated amine solution can be used, the phosgene excess is kept low, the energy consumption is drastically reduced and no circulating pumps are required for recirculating the reaction mixture. Thus, the object of the present invention is to prepare organic isocyanate in high yields while avoiding the above mentioned disadvantages of the previously known processes.

DETAILED DESCRIPTION OF THE INVENTION

The present invention provides a process for the continuous preparation of organic isocyanates by reacting primary organic amines with phosgene in an organic solvent, wherein the reaction mixture is circulated by means of a bubble column at a temperature of from 60° to 100° C., and the ratio of the quantity of circulated amine reaction products to the quantity of amine supplied is from 100:1 to 5:1, preferably 80:1 to 10:1.

The primary organic amines introduced into the process according to the invention can be any monofunctional or polyfunctional, aliphatic, cycloaliphatic or aromatic amines. Suitable examples of such compounds includes, for example, toluylenediamine, diaminodiphenylmethane, 1,5-diaminonaphthalene, chlorinated anilines, such as 3,4-dichloroaniline, triphenylmethanetriamine, aniline and derivatives. In particular, it is preferred to use toluylenediamine or diaminodiphenylmethane. The amines may be used either as pure isomers or as isomeric mixtures.

In the process according to the invention, the amines to be used are added in solution to the reaction mixture. As a rule, the primary organic amines are used as a 10 to 50 wt. %, preferably 20 to 40 wt. %, solution in an organic solvent.

The inert, organic solvents used in this process can be virtually any of the known organic solvents for the phosgenation process. Particularly suitable solvents are chlorobenzene and/or o-dichloro-benzene.

When the amine solution is added to the reaction mixture, which consists essentially of organic solvent, amine hydrochloride, carbamic acid chloride, isocyanate and phosgene, it is advantageous to inject the amine solution into the reaction mixture by means of a nozzle such that the amine flows in the same direction as the circulated reaction mixture flows. The amine is discharged from the nozzle at a discharge velocity of from 5 to 50 m/s, preferably of from 20 to 40 m/s.

In the process according to the invention, it is possible to add phosgene to the reaction mixture either in gaseous form or dissolved in the above-mentioned inert organic solvents. The quantity of phosgene to be added in the process is from 110 to 300%, preferably from 150 to 250%, based on the quantity of phosgene that is stoichiometrically required for the conversion of the amine to the isocyanate.

The process of the invention is designed in such a way that the reaction mixture is circulated in a vessel by means of a bubble column, which arises due to hydrogen chloride formed and excess phosgene as a result of the reaction of amine with phosgene dissolved in the reaction mixture. It is important that the ratio of the quantity of the circulated amine reaction products to the quantity of amine supplied is from 100:1 to 5:1, preferably 80:1 to 10:1. The phrase "quantity of the circulated amine reaction products" refers to the total quantity of the reaction products of the used amine (such as for example amine hydrochloride, carbamic acid chloride, isocyanate).

For reasons of economy in processing, it is advantageous if the phosgenation of the amines to the corresponding isocyanates is carried out not in one step but in a further processing stage. In this further processing stage, the amine hydrochloride present in the reaction mixture is reacted with phosgene, with this reaction being carried out below the temperature required for the complete decomposition of carbamic acid chloride, and the carbamic acid chloride formed is then decomposed in the presence of phosgene to form the corresponding isocyanates.

The residence times of the reaction mixture in the reaction vessel are usually about 15 minutes to 4 hours. In the processing variant described immediately above, the residence time in the reaction vessel can be shortened considerably if, as discussed above, amine hydrochloride present in the reaction mixture is further reacted with phosgene in an additional processing stage.

The process according to the invention is preferably carried out in a loop reactor, with the gas lift by the bubble column being arranged either inside or outside the reaction vessel (reactor tower). The process according to the invention may, of course, also be carried out in reactors of a different construction. Although in the construction of other reactors, care must be taken to ensure that the reaction mixture is circulated by means of a bubble column and that a definite ratio of circulated reaction mixture to quantity of organic amines supplied is maintained.

The process according to the invention is advantageously carried out at slightly lowered to slightly raised pressure. Operation of the process is generally within the pressure range of from 0.5 bar to 5 bar, preferably from 1 bar to 3 bar.

The working up of the reaction mixture obtained is carried out in a conventional manner such as, for example, by freeing the reaction mixture from excess phosgene, recovering the organic solvent by distillation and optionally distilling the reaction mixture repeatedly for isolation of the isocyanates. The concentrated, solvent-free crude product can be further processed directly to form polyurethanes.

The yields of organic isocyanates obtained by the process according to the invention are generally from 90 to 99% of theoretical yields.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

A loop reactor was used, consisting of a tower 2 m in height and 50 mm in diameter and having a head 80 mm in diameter for the separation of gas, with an external circulation tube of 15 mm in diameter. Within this tower, was a secondary reaction tube of 15 mm in diameter that was arranged centrally in the tower over its entire height and led out into the reactor head and to a thin-film evaporator of 40 mm in diameter and 0.5 m in height. The reactor head was additionally equipped with a waste gas tube, which likewise led up to the thin-film evaporator. Down below, at the level of the tower base, over a length of 50 mm, the circulation tube had a taper of 6 mm into which a capillary tube of 0.17 mm, with an opening upwards, projected from below. An annular passage for the gas feed was arranged around the taper of the circulation tube at the upper end.

The circulation tube was introduced into the reactor head tangentially at the top. The loop reactor, including the secondary reaction tube, had a useful volume of 5.4 l. The tower was surrounded by an insulating jacket and the circulation tube was surrounded by a heating jacket.

To start up the process, a 3% phosgene solution in monochlorobenzene, which was already at the reaction temperature of 80° C., was placed in the loop reactor. The start-up time was at least four times the residence time. The thin-film evaporator was operated at a jacket temperature of 150° C. A phosgene stream was passed at a rate of 1,800 g/h to the gas feed. Diaminodiphenylmethane having a viscosity of 88 mPa.s (in a mixture, which was formed by the condensation of aniline and formaldehyde) was mixed with three parts by weight of monochlorobenzene, and was injected by means of a piston pump at a nozzle discharge velocity of about 40 m/s through the capillary tube into the loop reactor. The reaction mixture circulated by the bubble column, which was formed in the circulation tube by liberated hydrogen chloride gas and excess phosgene, had a mass flow rate of 180 kg/h. In this process, after separation of the solvent, 208 g of a mixture of 4,4'-diisocyanatodiphenylmethane with its isomers and homologues, having a viscosity of 71 mPa.s and an NCO content of 32.1% wt. NCO, was obtained per hour per liter of useful reactor volume.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the continuous preparation of organic isocyanates comprising reacting at least one primary organic amine with phosgene in the presence of an inert, organic solvent, the improvement wherein the reaction mixture is circulated by means of a bubble column at a temperature of about 60° to 100° C., and the ratio of the quantity of circulated amine reaction products to the quantity of supplied amine is from 100:1 to 5:1.

2. The process of claim 1, wherein the reaction is carried out in a loop reactor, and said bubble column is located either inside or outside of the reactor.

3. The process of claim 1, wherein the amine hydrochloride present in the reaction mixture is reacted with phosgene in an additional processing step at a temperature lower than the temperature at which carbamic acid chloride completely decomposes.

4. The process of claim 1, wherein said primary organic amine is present as a 10 to 50% wt. solution in an organic solvent.

5. The process of claim 4, wherein said amine solution is injected into the reaction mixture by means of a nozzle at a nozzle discharge velocity of from 5 to 50 m/s, said nozzle being located such that the direction of flow of the amine solution is the same direction of flow as the circulating reaction mixture.

* * * * *